(12) United States Patent
Ohya et al.

(10) Patent No.: US 9,021,858 B2
(45) Date of Patent: May 5, 2015

(54) APPARATUS FOR TESTING WATER HAMMER STRENGTH OF GLASS BOTTLE

(75) Inventors: Yuuichi Ohya, Kanagawa (JP); Shinji Saitoh, Tokyo (JP); Johshiroh Yamaguchi, Tokyo (JP); Yosuke Ueda, Tokyo (JP)

(73) Assignee: Toyo Glass Co., Ltd., Tokyo (JP)

( * ) Notice: Subject to any disclaimer, the term of this patent is extended or adjusted under 35 U.S.C. 154(b) by 327 days.

(21) Appl. No.: 13/576,766

(22) PCT Filed: Mar. 4, 2010

(86) PCT No.: PCT/JP2010/053555
§ 371 (c)(1),
(2), (4) Date: Aug. 2, 2012

(87) PCT Pub. No.: WO2011/099169
PCT Pub. Date: Aug. 18, 2011

(65) Prior Publication Data
US 2012/0312070 A1    Dec. 13, 2012

(30) Foreign Application Priority Data

Feb. 12, 2010  (JP) .................................. 2010-028566

(51) Int. Cl.
*G01N 3/303*  (2006.01)
*G01N 33/00*  (2006.01)

(52) U.S. Cl.
CPC ........ *G01N 3/303* (2013.01); *G01N 2033/0081* (2013.01)

(58) Field of Classification Search
CPC .. G01N 2033/0081; G01N 3/303; G01N 3/30
USPC ............. 73/12.06, 12.08, 12.09, 12.13, 12.04
See application file for complete search history.

(56) References Cited

U.S. PATENT DOCUMENTS

| 2,498,291 | A | * | 2/1950 | Nadai | .......................... 73/12.09 |
| 3,254,524 | A | * | 6/1966 | Tannenberg | ................. 73/12.08 |

(Continued)

FOREIGN PATENT DOCUMENTS

| CN | 2656993 | 11/2004 |
| JP | 8-145837 | 6/1996 |

(Continued)

OTHER PUBLICATIONS

English Machine Translation of JP 08-145837, 1996, Kasai et al.*
Japanese Office Action issued Jul. 20, 2010, in corresponding Application No. 2010-028566 with English translation.

(Continued)

*Primary Examiner* — Lisa Caputo
*Assistant Examiner* — Philip Cotey
(74) *Attorney, Agent, or Firm* — Wenderoth, Lind & Ponack, L.L.P.

(57) ABSTRACT

An object is to prevent a bottle from being inclined when a weight is dropped, and to prevent cushion members from moving due to the impact applied when the bottle is inclined, thereby enabling efficient and correct measurement of the water hammer strength. An apparatus for testing the water hammer strength includes holding element that holds bottle filled with content and sealed with a cap at a position above the center of gravity thereof so as to suspend the bottle in the air, and the holding element is placed on cushion members placed on a fixing stage. A weight is then dropped onto the cap to measure the water hammer strength. The cushion members are compressed and deformed in advance using a compression element for forcing the holding element downward to solve the above-described problems.

8 Claims, 18 Drawing Sheets

(56) References Cited

U.S. PATENT DOCUMENTS

| | | | | |
|---|---|---|---|---|
| 3,402,593 | A | * | 9/1968 | Bresk et al. ............... 73/12.07 |
| 3,729,980 | A | * | 5/1973 | Johnson et al. ............ 73/12.08 |
| 2011/0120210 | A1 | * | 5/2011 | Saitoh et al. ............... 73/12.06 |

FOREIGN PATENT DOCUMENTS

| | | |
|---|---|---|
| JP | 2005-068707 | 3/2005 |
| JP | 2009-133708 | 6/2009 |

OTHER PUBLICATIONS

International Search Report issued May 18, 2010 in International (PCT) Application No. PCT/JP2010/053555.

Chinese Office Action (OA) issued Nov. 29, 2013 in corresponding Chinese Patent Application No. 201080063508.6, together with English translation of text portion thereof.

Chinese Search Report (SR) issued Nov. 29, 2013 in corresponding Chinese Patent Application No. 201080063508.6, together with English translation thereof.

* cited by examiner

APPARATUS FOR TESTING WATER HAMMER STRENGTH OF GLASS BOTTLE

TECHNICAL FIELD

The present invention relates to an apparatus for testing the water hammer strength of a glass bottle using a single glass bottle.

BACKGROUND ART

The water-hammer-strength test of glass bottles is defined by the "water-hammer test method" prescribed by Japan Glass Bottle Association. This defines the water-hammer test method for packaged glass bottles.

FIG. 18 is a diagram for explaining a test according to the above-mentioned definition. This test uses a drop testing machine 20 defined by "JIS Z 0202". A case of a lower dummy 23 (the same as a sample) is placed on a drop surface 21 (an iron plate having a thickness of 20 mm or more), and a case of a sample 24 is disposed thereon. A case of an upper dummy 25 (the same as the sample) is placed on a sample stage 22 of the drop testing machine 20. The lower dummy 23, the sample 24, and the upper dummy 25 are bottles filled with a predetermined amount of formal content according to a formal filling method and sealed with a predetermined cap, or other equivalents, which are packaged in a predetermined manner. Each case accommodates many glass bottles.

The sample stage is set at a predetermined drop height (the distance between the bottom surface of the upper dummy and the top surface of the sample), and the upper dummy is dropped onto the sample from a drop height of, for example, at first, 30 cm. The drop tests are repeated until a predetermined drop height is reached to see if any one of the glass bottles in the sample is damaged, while increasing the drop height by an increment of 5 cm (for a drop height of 60 cm or more, an increment of 10 cm is applied). The drop height at which any one of the sample bottles is damaged is regarded as the water hammer strength.

When the upper dummy 25 falls onto the sample 24, the case of the lower dummy 23 is deformed, and the glass bottles in the sample 24 are abruptly pushed downward. However, the content (liquid) of the glass bottles remains at the original position due to inertia, creating vacuum portions (vacuum bubbles) at the bottoms of the bottles. Immediately after that, the content abruptly falls onto the bottoms, which are in a vacuum state, causing a water hammer effect.

The "water-hammer test method" prescribed by Japan Glass Bottle Association is for measuring the water hammer strength of packaged glass bottles and is not for testing the water hammer strength of glass bottles themselves (the water hammer strength changes depending on the specifications of packages). Furthermore, because the test cannot be performed without preparing cartons, the test requires many products (about 10 cases). Thus, the water hammer strength evaluation cannot be performed in the test production in the design phase of bottle parisons. Moreover, the test requires considerable labor for tasks such as lifting the cartons, checking the bottles for damage, cleaning up of the damaged bottles, checking the cartons for damage, etc.

PTL 1 below proposes a technique that solves the above-described problems, enables measurement of the water hammer strength of glass bottles themselves with relative ease, and enables strength evaluation in the test production (in the design phase of bottle parisons).

This is a method for testing the water hammer strength of a glass bottle, in which holding element is provided on a fixing stage via a cushion member, the holding element holds the bottle filled with content and sealed with a cap at a position above the center of gravity thereof so as to suspend the bottle in the air, a weight is directly or indirectly dropped onto the cap to apply an impact to the bottle, and the weight is repeatedly dropped while gradually increasing the drop energy, thereby testing the water hammer strength of the bottle on the basis of the drop energy of the weight when the bottle is damaged.

When the weight is directly or indirectly dropped onto the cap, the cushion member is deformed, and the bottle is abruptly pushed downward, causing a water hammer effect. If the weight is dropped onto the bottle held at a position above the center of gravity thereof and suspended, the drop energy of the weight acts on the bottle efficiently. Thus, the drop energy of the weight is strongly associated with the impact applied to the bottle, making it possible to accurately know the water hammer strength of the bottle on the basis of the drop energy of the weight when the bottle is damaged.

CITATION LIST

Patent Literature

PTL 1: Japanese Unexamined Patent Application Publication No. 2009-133708

FIG. 17 is a diagram for explaining an example of the apparatus for testing the water hammer strength disclosed in PTL 1, showing a state in which a weight 5 has been dropped.

In this test apparatus, a base stage 6, a post 7, and a fixing stage 2 are formed as a single component. Four cushion members 3 are disposed around a through-hole 2a in the fixing stage 2, and holding element 4 is placed thereon. The cushion members 3 are made of elastic members composed of rubber, soft resin, or the like. The holding element holds a bottle 1 that is filled with content and sealed with a cap 1b at a position above the center of gravity thereof (in this case, below a bead 1a) and suspends the bottle in the air. The weight 5 is provided above the cap 1b of the bottle 1.

When the weight 5 is dropped onto the cap 1b of the bottle, the cushion members 3 are compressed and deformed due to the impact, and the bottle 1 is abruptly pushed downward, causing a water hammer effect.

At this time, because the cushion members 3 are very soft, the compression and deformation thereof do not always occur in the vertical direction, and, as shown in FIG. 17, middle parts or the like may be deformed in the horizontal direction (out-of-plane deformation). Because the extent of the out-of-plane deformation usually differs among the cushion members, the bottle 1 may be inclined, as shown in FIG. 17. Furthermore, the bottle 1 is sometimes significantly inclined, causing the cushion members 3 to move (in a direction of arrow A) or jump out of the apparatus.

It cannot be said that the measured water hammer strength is correct if the bottle is significantly inclined or if the cushion members 3 jump out of the apparatus when the weight 5 is dropped. Thus, in such a case, the cushion members have to be returned to the original positions and the measurement has to be performed again.

SUMMARY OF THE INVENTION

An object of the present invention is to prevent the bottle from being inclined when the weight 5 is dropped, and to prevent the cushion members 3 from moving due to the impact. Thus, efficient and correct measurement of the water hammer strength can be achieved.

Solution to Problem

The present invention is an apparatus for testing the water hammer strength, the apparatus including: a fixing stage; a cushion member placed on the fixing stage; a holding element that is placed on the cushion member and holds a bottle filled with content and sealed with a cap at a position above the center of gravity thereof so as to suspend the bottle in the air; and a weight to be dropped onto the cap to apply an impact to the bottle, wherein push-down means (a compression element) for forcibly pushing the holding element downward is provided, and wherein the cushion member is compressed and deformed by the compression element.

By compressing and deforming the cushion member in advance using the push-down means (compression element), the cushion member becomes less susceptible to out-of-plane deformation when the weight 5 is dropped. As a result, the inclination of the bottle is considerably reduced. The movement of the cushion member is also reduced.

The compression element may have any mechanism as long as it can forcibly push the holding element downward. Besides the mechanism descried below, compression element utilizing a known mechanism, such as a clamp or a vice, may be employed.

More specifically, the compression element may be a bolt screwed to the fixing stage from a top surface side of the holding element.

By providing a bolt hole in the holding element, by providing a female screw hole in the fixing stage, and by screwing the bolt to the fixing stage from the top surface side of the holding element, it is possible to easily push down the holding element to compress and deform the cushion member. The extent by which the holding element is pushed downward may be easily adjusted by changing the tightness of the bolt.

The cushion member may be formed of a plurality of cushion bodies bonded together with a non-cushioning plate therebetween.

By doing so, the cushion member becomes even less susceptible to out-of-plane deformation when the weight 5 is dropped, and, as a result, the inclination of the bottle is further reduced, and the movement of the cushion member is also further reduced.

Examples of the material of the non-cushioning plate include plastic, metal, and wood, which are less likely to be deformed than the cushion member.

A non-slip sheet may be disposed between the fixing stage and the cushion member and between the cushion member and the holding element.

Because the cushion member experiences significant deformation during the tests, the cushion member is deteriorated (cause cracks) after being subjected to impact several hundreds of times. Thus, the cushion member is an expendable member that requires replacement every time it is deteriorated. Therefore, the cushion member cannot be securely bonded to the fixing stage and the holding element. To prevent the cushion member from falling off, a non-slip sheet having a high coefficient of friction may be disposed between the fixing stage and the cushion member and between the cushion member and the holding element.

By doing so, the cushion member becomes even less likely to move when the weight 5 is dropped.

A sheet having good non-slip effect, such as a natural rubber sheet or a silicone rubber sheet, may be used as the non-slip sheet. The appropriate thickness of the sheet is from about 0.3 mm to 1 mm.

Furthermore, the present invention is the apparatus for testing the water hammer strength, wherein the fixing stage and/or the holding element has a recess in a surface in contact with the cushion member, wherein the non-slip sheet is provided in the recess, and wherein the cushion member is embedded in the recess by 0.2 mm to 0.8 mm.

By doing so, the non-slip sheet and the cushion member do not come off from the recess, and the movement thereof can be prevented. Although the recess may be provided in only one of the fixing stage and the holding element, it is desirable that the recess be provided in both of them.

The appropriate amount by which the upper end or the lower end of the cushion member is embedded in the recess (y in FIG. 7) is from about 0.2 mm to 0.8 mm. If it is smaller than 0.2 mm, the cushion member may come off from the recess and move, and if it is larger than 0.8 mm, the cushion member may be cracked when it collides with the outer periphery of the recess, degrading the endurance of the cushion member, which is undesirable.

Note that the appropriate value for the distance between the cushion member and the outer periphery of the recess in the horizontal direction (x in FIG. 7) is 0.1 mm to 0.5 mm. If it is smaller than 0.1 mm, due to the collision between the cushion member and the outer periphery of the recess, the cushion member tends to cause a crack at the corresponding part, and if it is larger than 0.5 mm, the cushion member moves significantly, which may allow the bottle to be inclined.

Furthermore, the present invention is the apparatus for testing the water hammer strength, wherein the cushion member is formed of a plurality of cushion bodies bonded together with a non-cushioning plate therebetween and non-cushioning plates bonded to the upper and lower ends thereof. The fixing stage and/or the holding element has a recess in a surface in contact with the cushion member, and the plate at the upper end and/or the plate at the lower end is disposed in the recess.

By bonding the non-cushioning plates to the upper and lower ends of the cushion member, the soft cushion body does not collide with the outer periphery of the recess when the cushion member moves, whereby the endurance of the cushion member is maintained. Furthermore, because the upper and lower ends of the cushion member are the non-cushioning plates, the cushion member will not move beyond the recess, whereby the movement of the cushion member is reliably limited.

Furthermore, the present invention is the apparatus for testing the water hammer strength, wherein the cushion member is formed of a plurality of cushion bodies bonded together with a non-cushioning plate therebetween and non-cushioning plates bonded to the upper and lower ends thereof. The plate at the upper end and/or the plate at the lower end has a hole in the top or bottom surface thereof, and the fixing stage and/or the holding element has a projection that fits into the hole in the surface in contact with the cushion member.

Because the hole in the cushion member and the projection on the fixing stage or the holding element fit together, the movement of the cushion member is prevented.

The fixing stage and the holding element do not need to have a recess and, thus, can be reduced in thickness.

Advantageous Effects of Invention

With the apparatus for testing the water hammer strength of the present invention, the cushion member is less susceptible to out-of-plane deformation and is less likely to move when the weight is dropped. Thus, it is possible to efficiently and correctly measure the water hammer strength.

DETAILED DESCRIPTION OF THE INVENTION EMBODIMENTS

Figure 1:
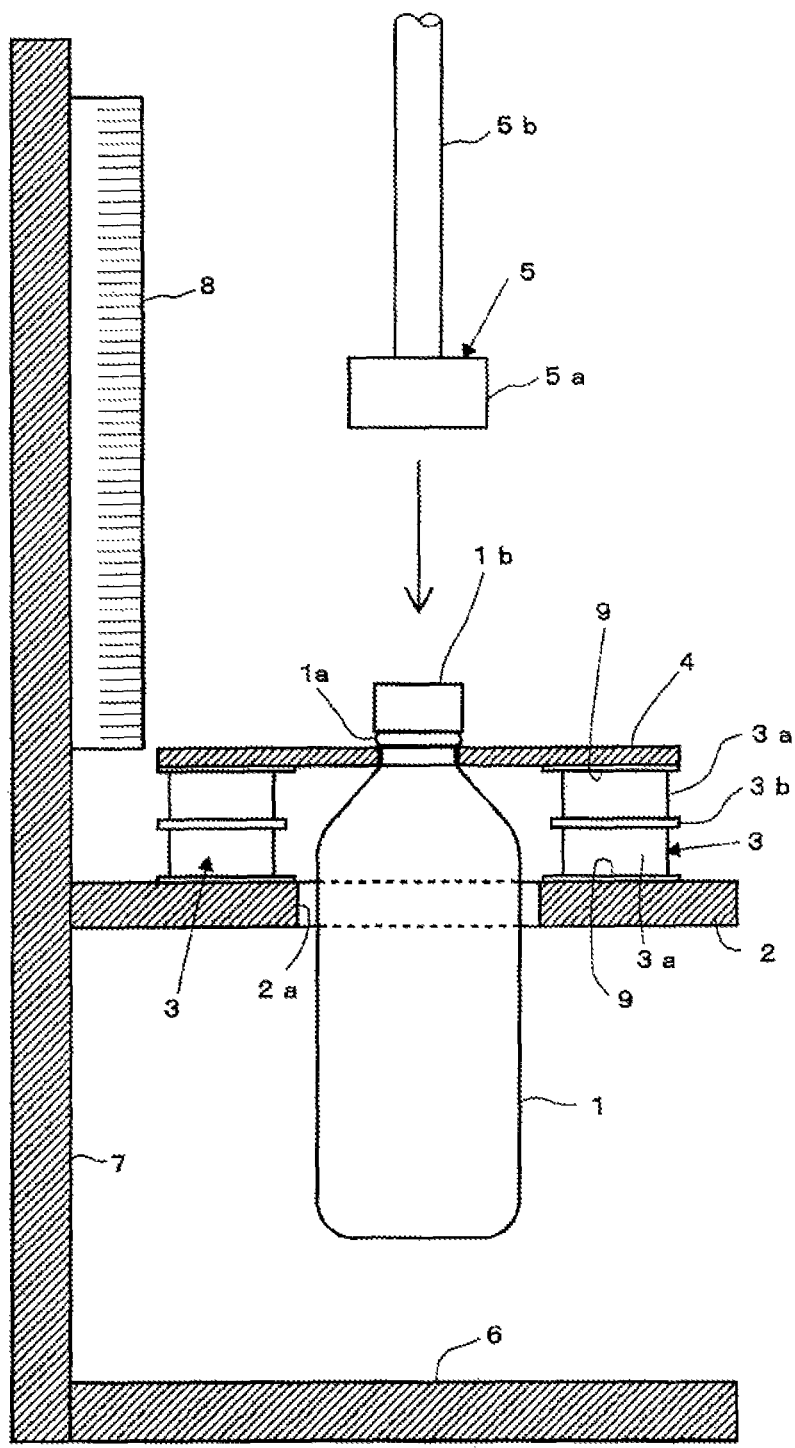
FIG. 1 is a cross-sectional diagram for explaining a test apparatus according to an embodiment.

FIGS. 1 to 5 relate to a test apparatus according to an embodiment. A base stage 6, a post 7, and a fixing stage 2 are formed as a single component by processing a steel plate. The post 7 stands upright from the base stage 6 so as to form an L shape, and the fixing stage 2 is formed so as to project from the middle of the post 7. The fixing stage 2 has a through-hole 2a into which a body of a bottle 1 can be inserted.

Cushion members 3 are placed at four corners around the through-hole 2a in the fixing stage 2, and a holding element 4 is placed thereon.

Figure 14:
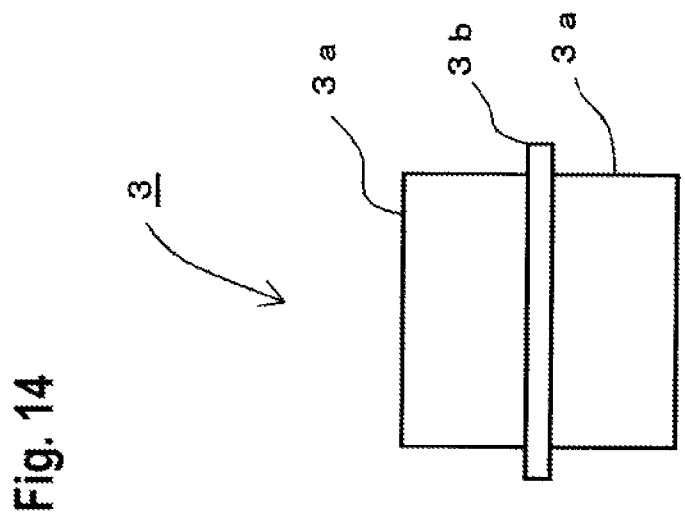
FIG. 14 is a side view of an exemplary cushion member.
Figure 15:
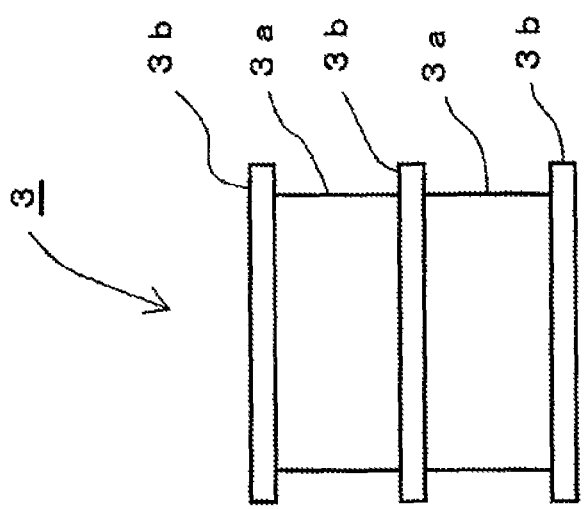
FIG. 15 is a side view of an exemplary cushion member.

As shown in FIG. 14, each cushion member 3 is formed of two cushion bodies 3a and a plate 3b disposed therebetween, which are securely bonded together. The cushion bodies 3a are made of elastic members composed of rubber, soft resin, or the like. In this case, the cushion bodies 3a are made of soft gel-like members mainly composed of silicone (JIS K 2207, with a penetration of 55 and a Young's modulus of 119.5 kPa) and having a size of 20 mm×20 mm×10 mm. The plate 3b is made of a non-cushioning material less likely to be deformed than the cushion bodies 3a. Although non-cushioning plastic (i.e., plastic containing no foaming agent), metal, or a wood plate may be used, the plate 3b in this case is made of polycarbonate and has a size of 24 mm×24 mm×2 mm.

Non-slip sheets 9 are disposed between the fixing stage 2 and the cushion members 3, and between the cushion members 3 and the holding element 4. The non-slip sheets 9 are silicone rubber sheets having a thickness of 0.5 mm. The non-slip sheets 9 are bonded to the fixing stage 2 and the holding element 4.

The holding element 4 holds the bottle 1 filled with content and sealed with a cap at a position above the center of gravity thereof so as to suspend the bottle in the air. The material and shape of the holding element 4 are not specifically limited as long as it can securely hold the bottle 1 and it can be placed on the cushion members 3. For example, although the holding element 4 having various mechanisms, as disclosed in PTL 1, may be used, these mechanisms are omitted in the drawings of the present invention, and the glass bottle 1 is supported at a part immediately below the bead 1a by a through-hole 4a provided in the central part.

Although it is only necessary that the bottle 1 filled with content and sealed with a cap is held at a position above the center of gravity thereof, it is most desirable that the bottle 1 be held at a neck (immediately below a mouth or the bead).

Figure 2:
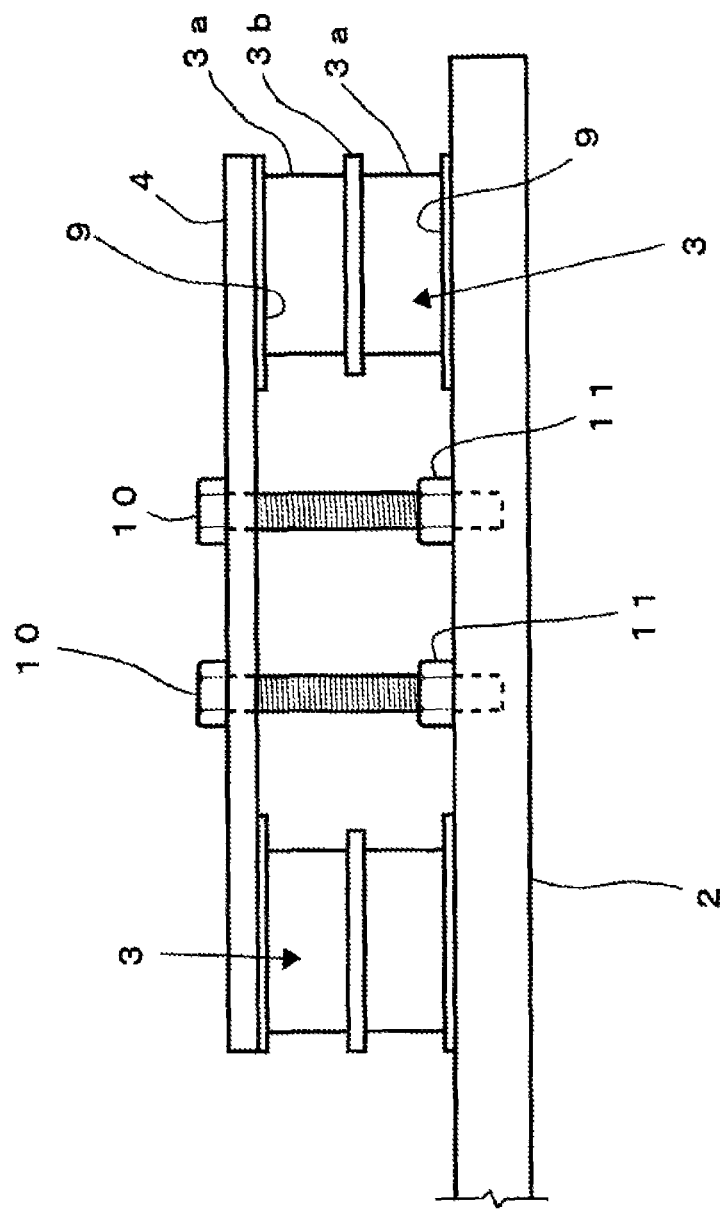
FIG. 2 is a side view of a fixing stage, cushion members, and holding element.
Figure 3:
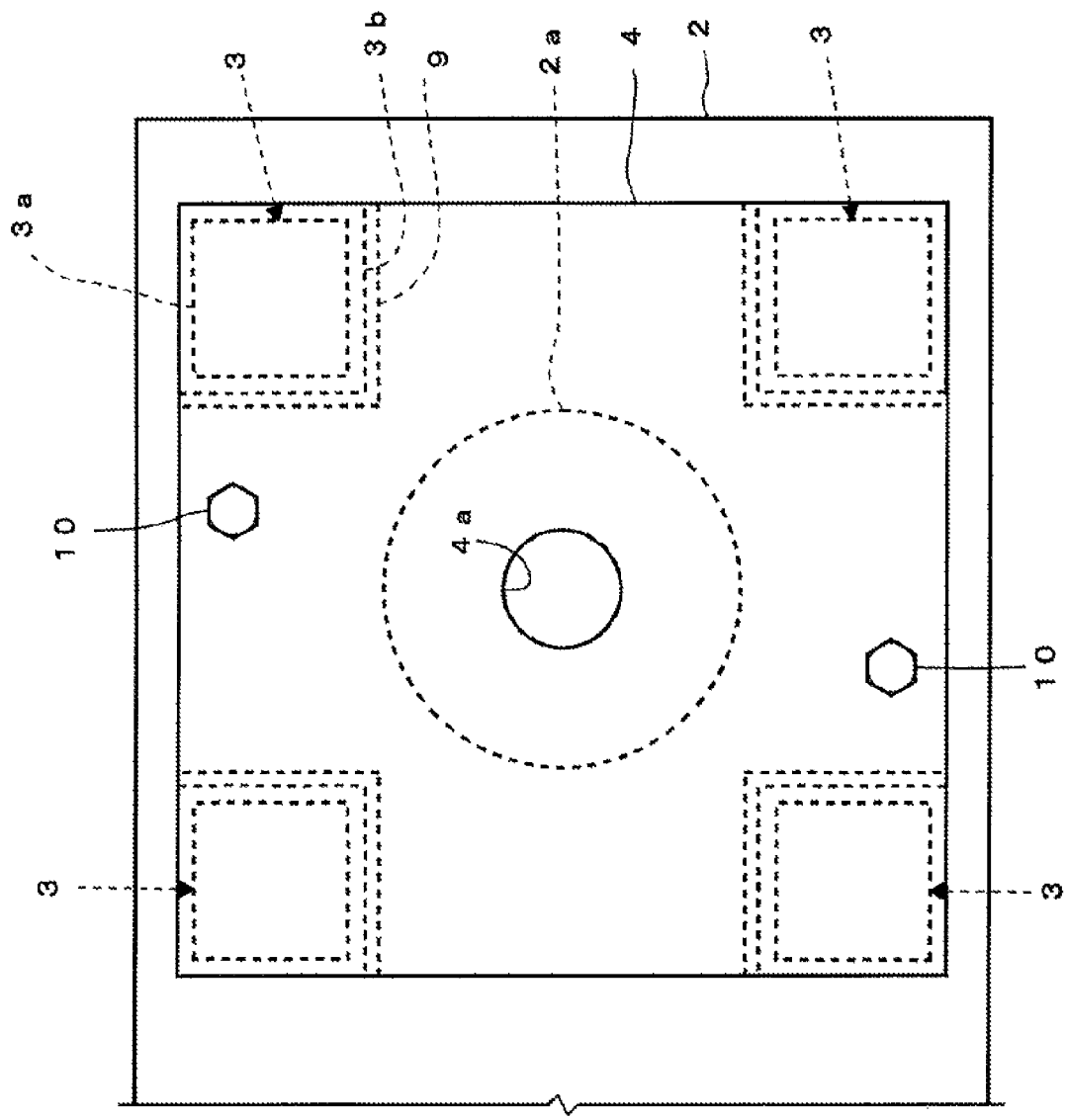
FIG. 3 is a plan view of the fixing stage, the cushion members, and the holding element.
Figure 4:
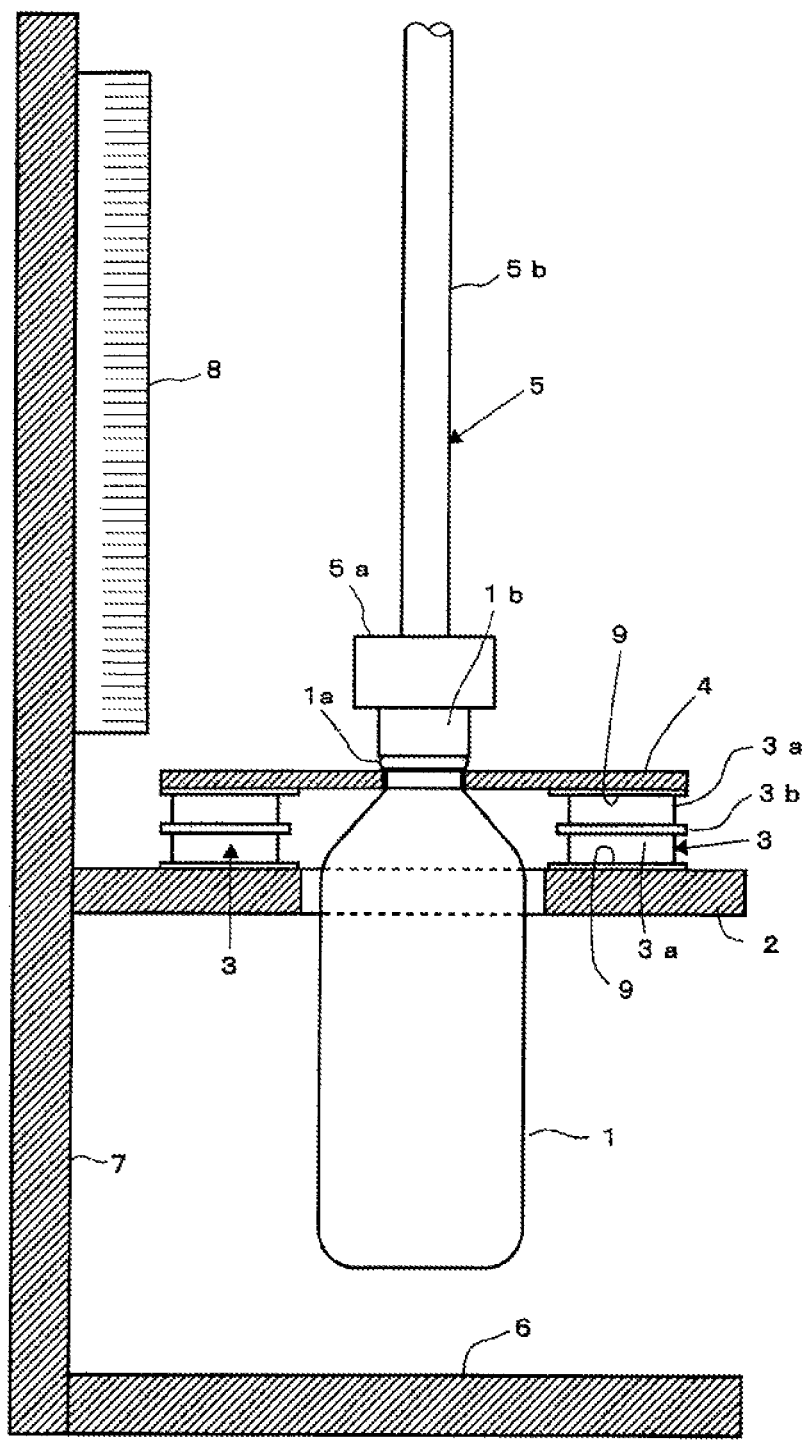
FIG. 4 is a cross-sectional diagram for explaining the test apparatus when the weight is dropped.
Figure 5:
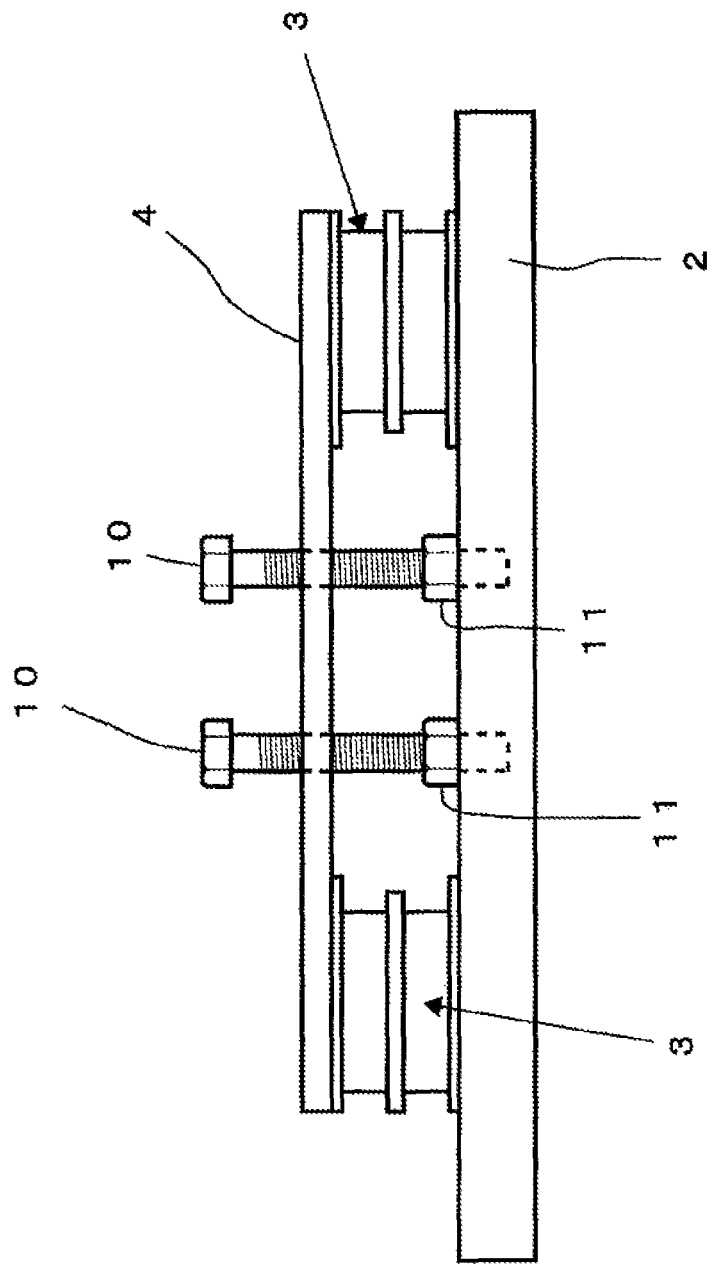
FIG. 5 is a side view of the fixing stage, the cushion members, and the holding element when the weight is dropped.

The holding element 4 has two bolt holes, and the fixing stage 2 has two corresponding female screw holes. A compression element is formed by screwing bolts 10 with the female screw holes in the fixing stage 2 from the top surface side of the holding element 4. Thus, the cushion members 3 are compressed and deformed (FIGS. 2 and 3). Nuts 11 prevent the bolts 10 from loosening. The cushion members 3, which originally have a total thickness of 22 mm, are compressed by the compression element to a thickness of 20.5 mm by forcibly pushing the holding element 4 downward with the bolts 10.

The weight 5 is provided above the cap 1b of the bottle 1. The weight 5, which is formed of a shaft 5b and a weight body 5a provided at the lower end thereof, is formed so as to protrude from the post 7 and is capable of moving vertically upward and downward along a guide (not shown) having an insertion hole through which the shaft 5b extends. The weight 5, held at a desired height by a stopper (not shown), falls right onto the cap 1b by removing the stopper.

The post 7 is marked with a scale 8 so that the height of the weight can be easily known.

When the weight 5 falls right onto the cap 1b, the cushion members 3 are deformed due to the drop energy thereof, and the holding element 4 and the bottle 1 are abruptly pushed downward (FIGS. 4 and 5), causing a water hammer effect.

Because the bolts 10 slide in the bolt holes in the holding element 4 at this time, the downward movement of the holding element 4 is not blocked. Furthermore, because the bolts 10 guide the downward movement of the holding element 4, the holding element 4 moves downward always vertically, and thus, is less likely to be inclined.

Because the cushion members 3 are compressed and deformed in advance and the plate 3b is provided in the middle thereof, the out-of-plane deformation caused when subjected to the impact of the weight 5 is very small. Moreover, because the bolts 10 guide the downward movement of the holding element 4, the inclinations of the holding element 4 and the bottle 1 are very small.

Whereas the inclination of the bottle 1 when the weight is dropped is 4° at the maximum and 2° on average with the conventional test apparatus 7, the inclination of the bottle 1 was reduced to a visually unrecognizable level in this embodiment.

In the measurement of the water hammer strength according to this embodiment, the weight is dropped several times while gradually increasing the drop energy, and the water hammer strength of the bottle is represented by the drop energy of the weight when the bottle is broken. The drop energy is adjusted by changing the weight and the drop height (the distance between the bottom surface of the weight and the top surface of the cap). The drop energy is mgh, where m is the mass of the weight, h is the drop height, and g is the acceleration of gravity.

Figure 6:
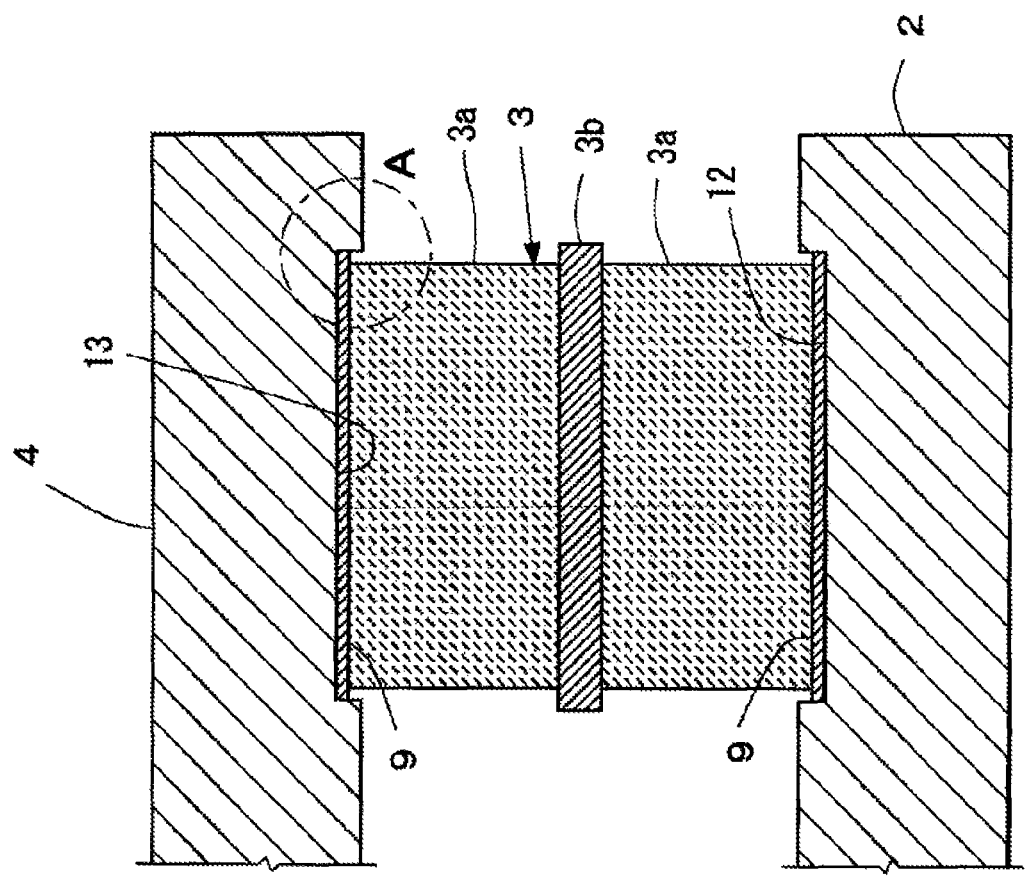
FIG. 6 is a vertical cross-sectional view of the relevant part of another embodiment.
Figure 7:
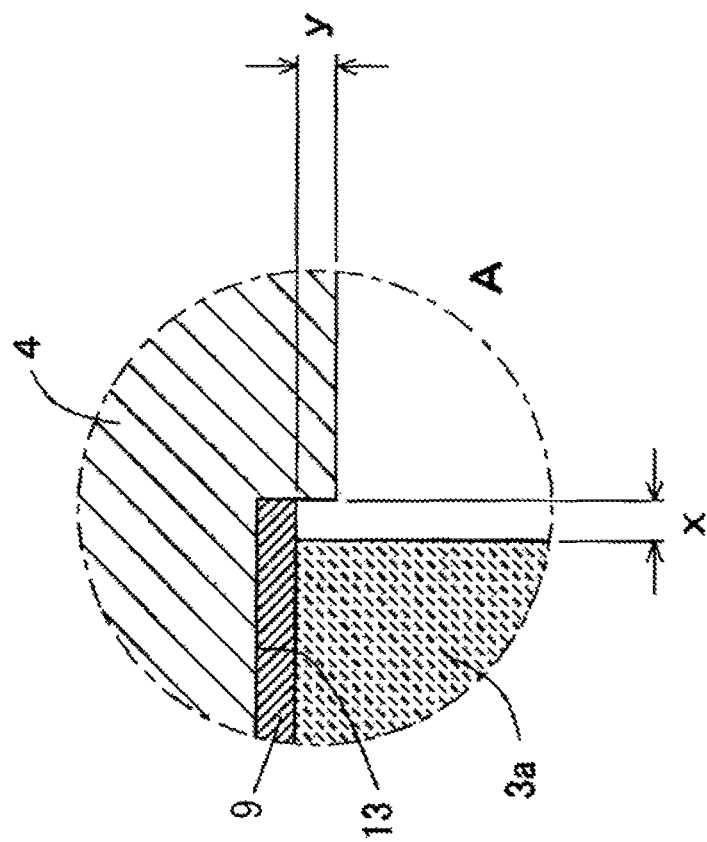
FIG. 7 is an enlarged view of part A in FIG. 6.
Figure 8:
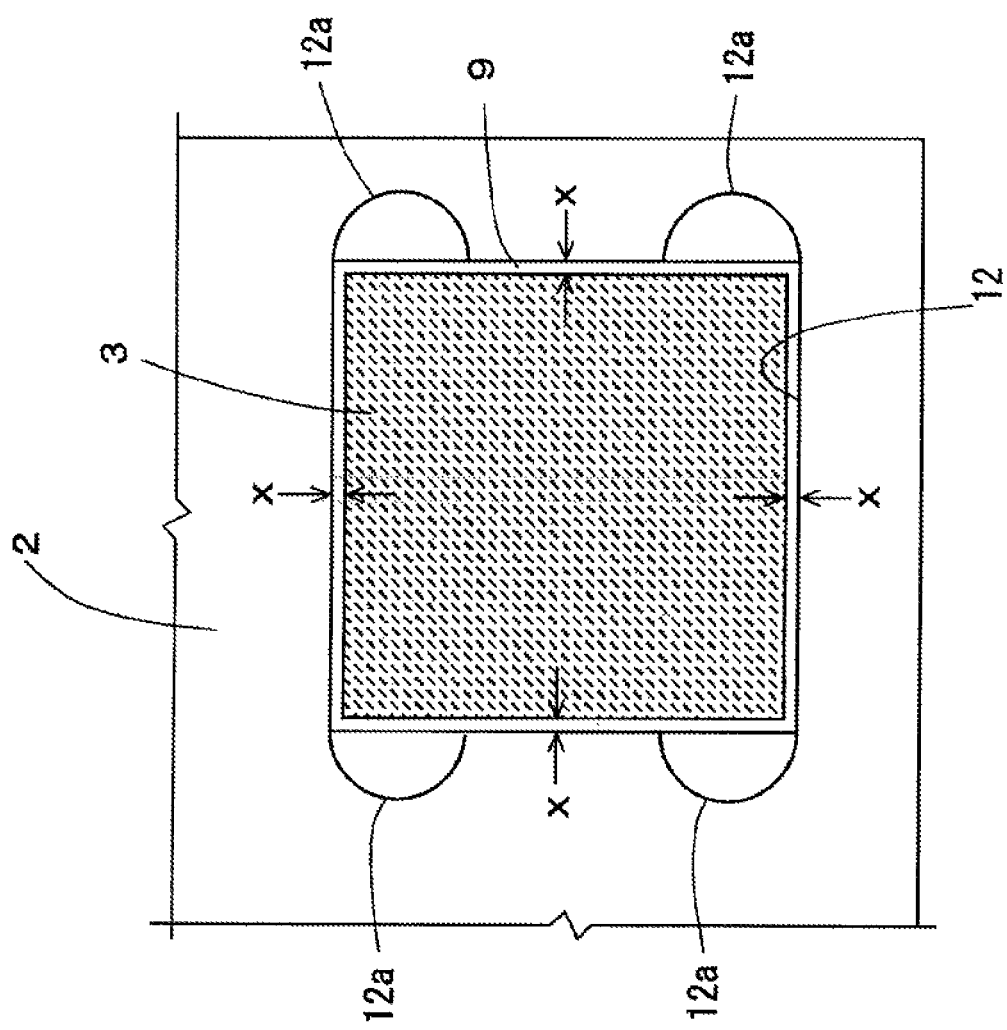
FIG. 8 is a horizontal cross-sectional view of the relevant part of the embodiment in FIG. 6.

FIGS. 6 to 8 show an embodiment in which the structure near the cushion members according to the embodiment in FIGS. 1 to 5 is changed. The other structures are the same as those according to the embodiment in FIGS. 1 to 5.

Similarly to the above-described embodiment, each cushion member 3 is formed of two cushion bodies 3a and a plate 3b disposed therebetween, which are securely bonded together (FIG. 14).

The non-slip sheets 9 are silicone rubber sheets having a thickness of 0.5 mm and a size of 20.6 mm×20.6 mm.

The fixing stage 2 and the holding element 4 have recesses 12 and 13 having a depth of 0.8 mm and a size of 20.6 mm×20.6 mm, in surfaces in contact with the cushion members. Semicircular portions of the recesses denoted by the reference numeral 12a in FIG. 8 are so-called milling cutter reliefs, which have to be provided to allow a milling cutter to cut the recesses. The shape of the recesses 12 and in the fixing stage 2 and the shape of recesses 13 in the holding element 4 are exactly identical.

The non-slip sheets 9 are placed in the recesses 12 and 13 in the fixing stage 2 and the holding element 4, and the cushion members 3 are disposed therebetween (FIG. 6). The cushion members 3, which originally have a total thickness of 22 mm, are compressed to a thickness of 20.5 mm by forcibly pushing the holding element 4 downward with the bolts 10.

As shown in FIG. 7, the cushion members 3 are embedded in the recesses 12 and 13 by a length of y. The appropriate value for the length y is from 0.2 mm to 0.8 mm, and in this embodiment, the length y is 0.3 mm. Furthermore, the appropriate value for the distance x between the cushion members 3 and the outer peripheries of the recesses 12 and 13 in the horizontal direction (except for the milling cutter relief portions) is from 0.1 mm to 0.5 mm, and in this embodiment, the distance x is 0.3 mm.

Figure 9:
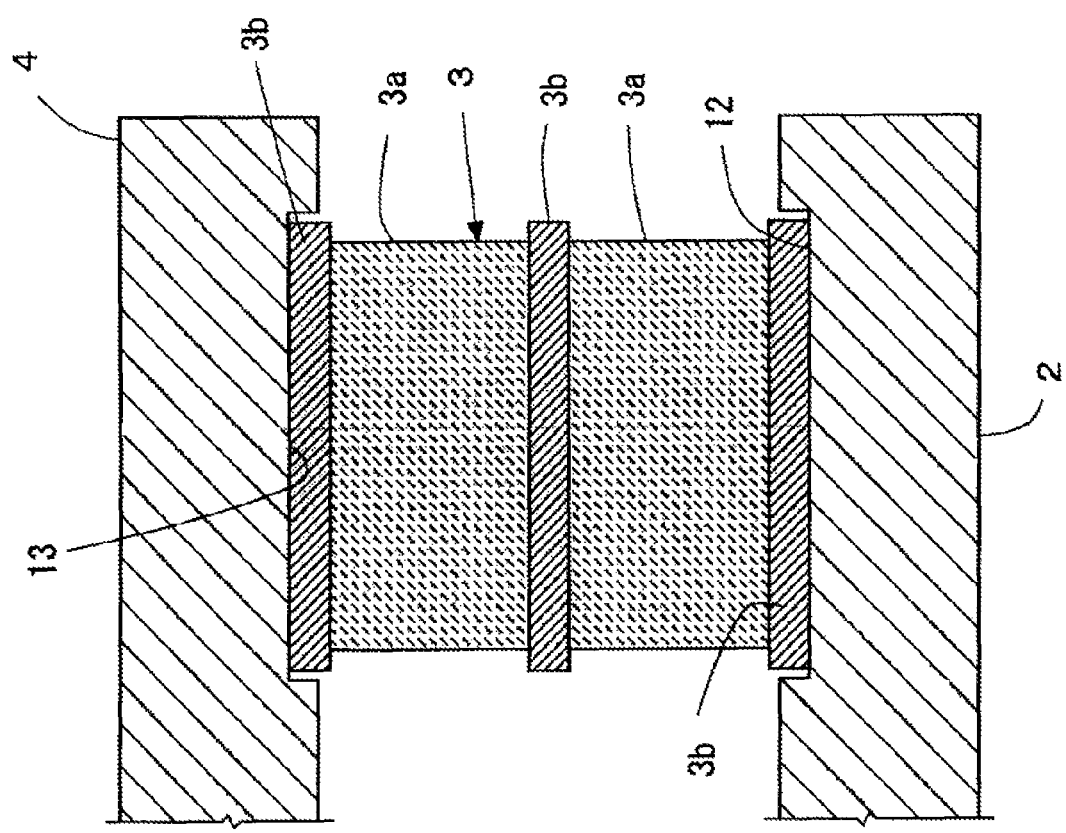
FIG. 9 is a vertical cross-sectional view of the relevant part of another embodiment.
Figure 10:
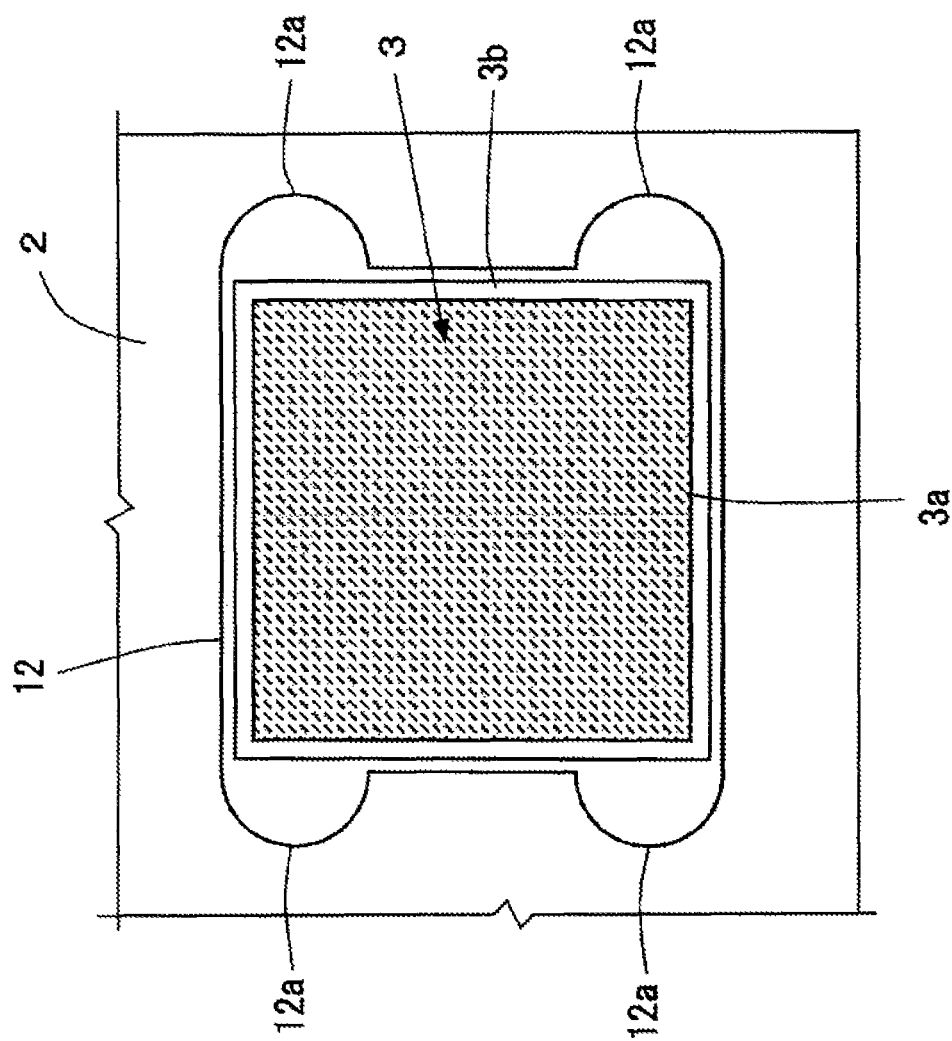
FIG. 10 is a horizontal cross-sectional view of the relevant part of the embodiment in FIG. 9.

FIGS. 9 and 10 also show an embodiment in which the structure near the cushion members according to the embodiment in FIGS. 1 to 5 is changed. The other structures are the same as those according to the embodiment in FIGS. 1 to 5.

As shown in FIG. 9, each cushion member 3 is formed of two cushion bodies 3a and a non-cushioning plate 3b bonded therebetween, and the same plates 3b securely bonded to the upper and lower ends thereof to form a single component. The cushion bodies 3a have a size of 20 mm×20 mm×10 mm, and the plates 3b have a size of 22 mm×22 mm×2 mm.

The fixing stage 2 and the holding element 4 have the recesses 12 having a depth of 1.5 mm and a size of 22.8 mm×22.8 mm in the surface in contact with the cushion members. Semicircular portions of the recesses denoted by the reference numeral 12a in FIG. 10 are so-called milling cutter reliefs, which have to be provided to allow a milling cutter to cut the recesses. The shape of the recesses 12 in the fixing stage 2 and the shape of recesses 13 in the holding element 4 are exactly identical.

The appropriate value for the distance between the plates 3b of the cushion members and the outer peripheries of the recesses 12 and 13 in the horizontal direction (except for the milling cutter relief portions) is from 0.1 mm to 0.5 mm, and in this embodiment, the distance is 0.4 mm.

The plates 3b at the ends of the cushion members are positioned in the recesses 12 and 13 in the fixing stage 2 and the holding element 4, and the cushion members 3 are disposed between the fixing stage 2 and the holding element 4 (FIG. 9). The cushion members 3, which originally have a total thickness of 26 mm, are compressed to a thickness of 24.5 mm by forcibly pushing the holding element 4 downward with the bolts 10.

Figure 11:
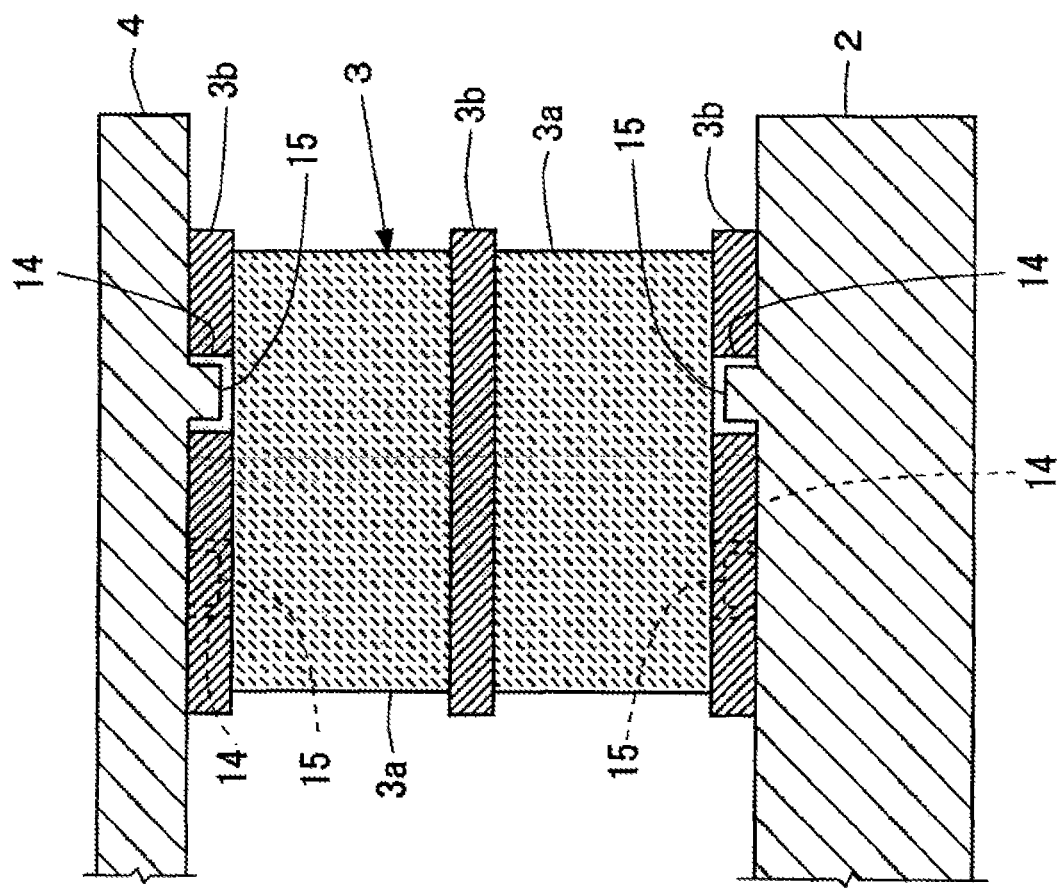
FIG. 11 is a vertical cross-sectional view of the relevant part of another embodiment.
Figure 12:
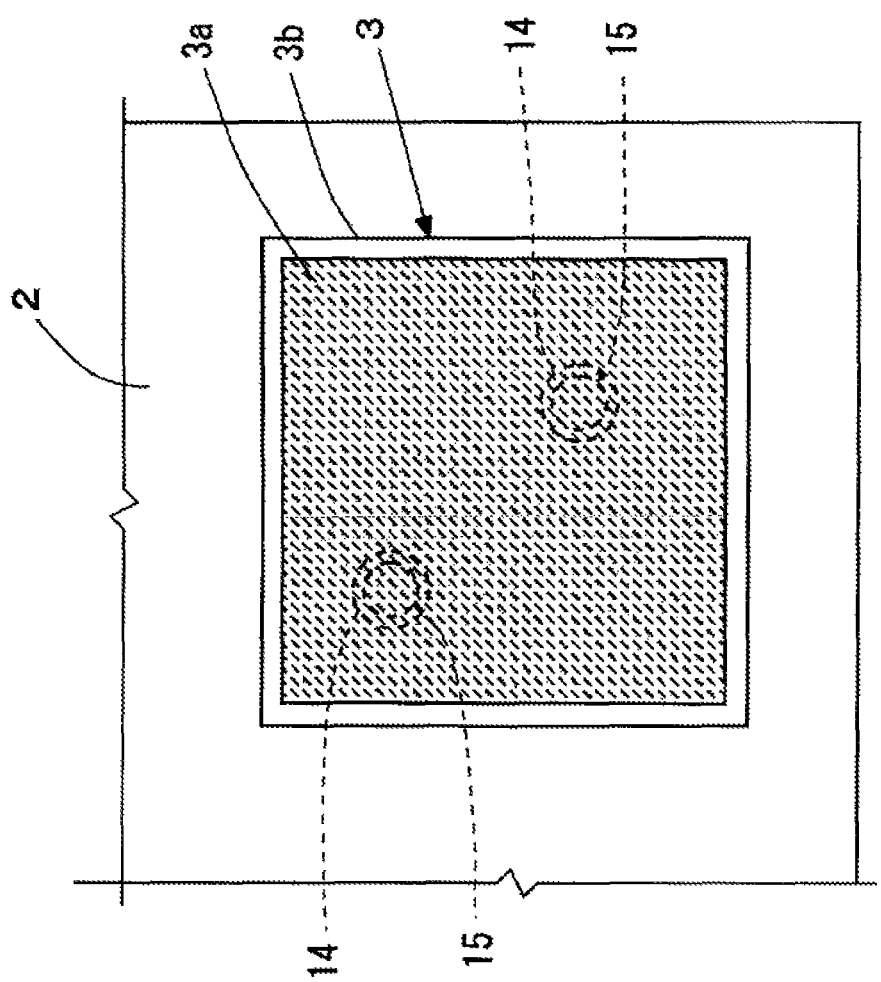
FIG. 12 is a horizontal cross-sectional view of the relevant part of the embodiment in FIG. 11.

FIGS. 11 and 12 also show an embodiment in which the structure near the cushion members according to the embodiment in FIGS. 1 to 5 is changed. The other structures are the same as those according to the embodiment in FIGS. 1 to 5.

Although the cushion members 3 are basically the same as those shown in FIGS. 9 and 10, the plates 3b at the upper and lower ends have two round holes 14 (having a diameter of 3.5 mm).

The fixing stage 2 and the holding element 4 have cylindrical projections 15 (having a diameter of 2.5 mm and a height of 1.5 mm) in the surface in contact with the cushion members, at positions corresponding to the holes 14. The appropriate value for the difference in diameter between the holes 14 and the projections 15 is from about 0.1 mm to 1 mm.

The cushion members 3 are disposed between the fixing stage 2 and the holding element 4. At this time, the projections 15 loosely fit into the holes 14 (FIG. 11). The cushion members 3, which originally have a total thickness of 26 mm, are compressed to a thickness of 24.5 mm by forcibly pushing the holding element 4 downward with the bolts 10.

Figure 13:
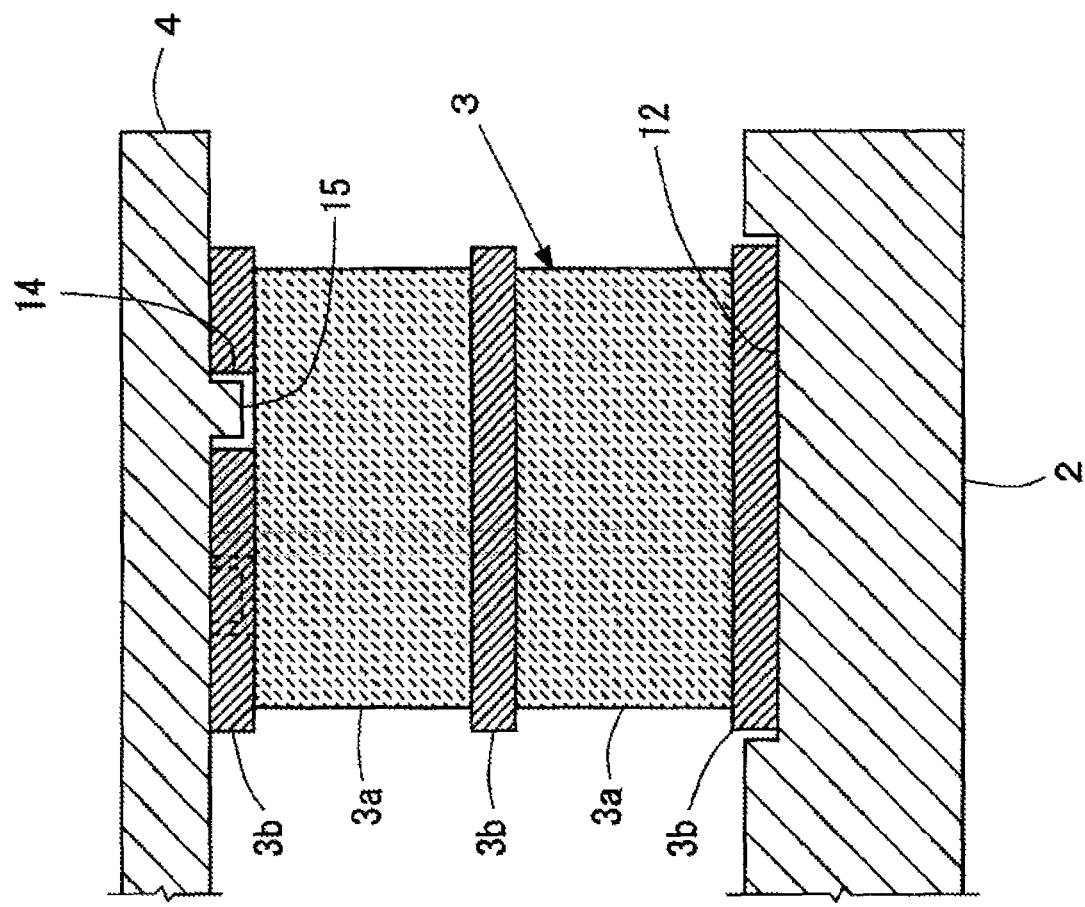
FIG. 13 is a vertical cross-sectional view of the relevant part of another embodiment.

FIG. 13 also shows an embodiment in which the structure near the cushion members according to the embodiment in FIGS. 1 to 5 is changed. The other structures are the same as those according to the embodiment in FIGS. 1 to 5.

In FIG. 13, although the cushion members 3 are basically the same as those shown in FIGS. 9 and 10, only the plates 3b at the upper end has two round holes 14 (having a diameter of 3.5 mm). This configuration is the same as that of the plate at the upper end of the cushion member shown in FIG. 11.

The fixing stage 2 has the recesses 12 having a depth of 1.5 mm and a size of 22.8 mm×22.8 mm in the surface in contact with the cushion members (top surface). This configuration is the same as that of the fixing stage shown in FIGS. 9 and 10.

The holding element 4 has the cylindrical projections 15 (having a diameter of 2.5 mm and a height of 1.5 mm) in the surface in contact with the cushion members (bottom surface), at positions corresponding to the holes 14. This configuration is the same as that of the holding element shown in FIG. 11.

The cushion members 3 are disposed between the fixing stage 2 and the holding element 4. The plates 3b at the lower ends of the cushion members 3 are positioned in the recesses 12 in the fixing stage 2, and the projections 15 loosely fit into the holes 14 at the upper ends of the cushion members. The cushion members 3, which originally have a total thickness of 26 mm, are compressed to a thickness of 24.5 mm by forcibly pushing the holding element 4 downward with the bolts 10.

This embodiment employs the structure of the embodiment in FIGS. 9 and 10 at the lower ends of the cushion members and the structure of the embodiment in FIGS. 11 and 12 at the upper ends.

Although each cushion member 3 is formed of two cushion bodies 3a securely bonded together with a non-cushioning plate 3b therebetween in the above-described embodiment, the number of the cushion bodies 3a may be three or more.

Figure 16:
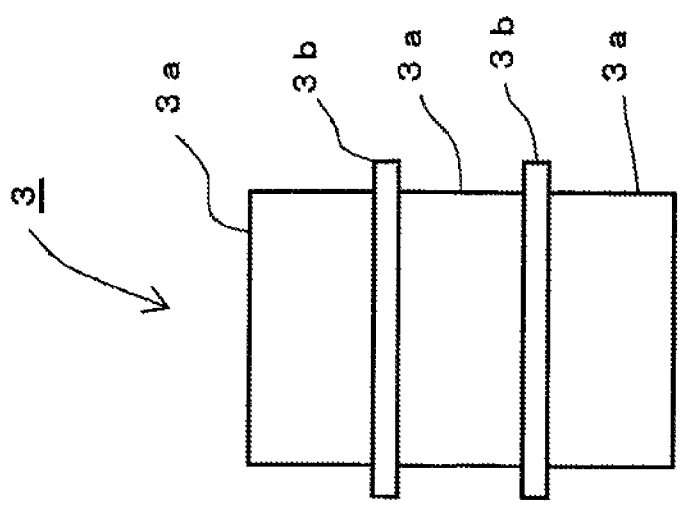
FIG. 16 is a side view of an exemplary cushion member.
Figure 17:
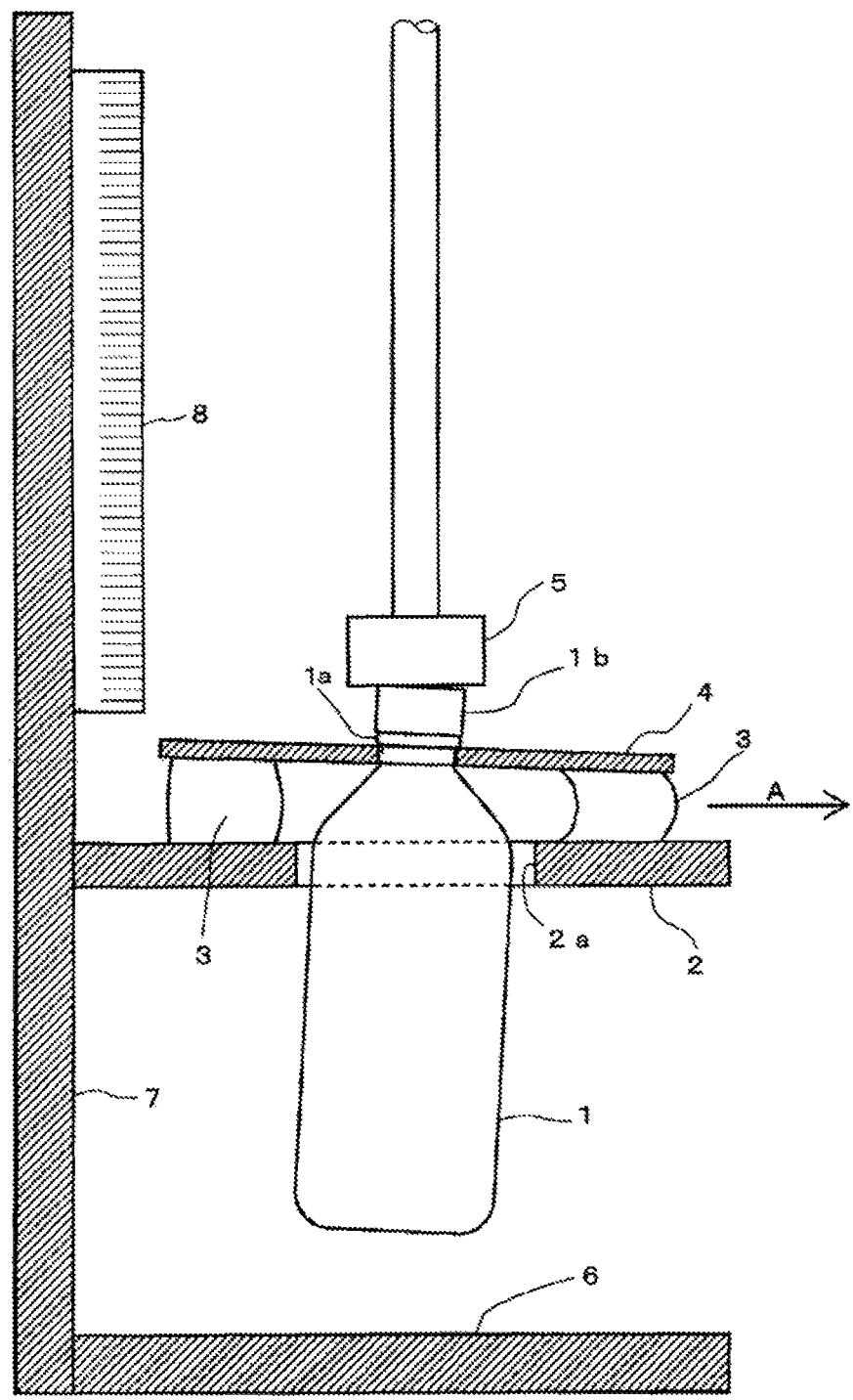
FIG. 17 is a cross-sectional diagram for explaining a conventional test apparatus.
Figure 18:
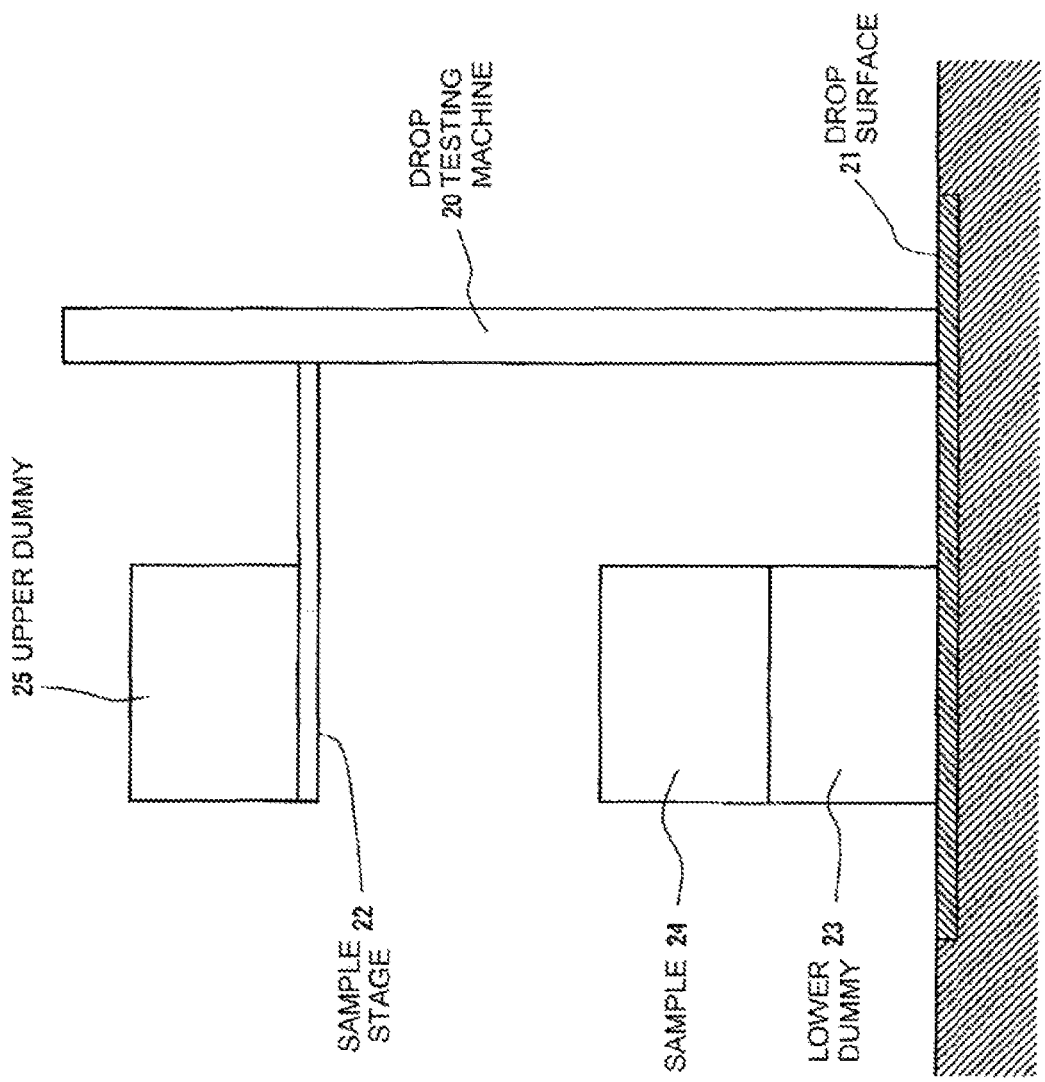
FIG. 18 is a diagram for explaining a method of testing packaged goods.

FIG. 16 shows an example in which three cushion bodies 3a are securely bonded together with non-cushioning plates 3b therebetween.

REFERENCE SIGNS LIST

1: glass bottle
1a: bead

1b: cap
2: fixing stage
3: cushion member
3a: body
3b: plate
4: holding element
5: weight
6: base stage
7: post
8: scale
9: non-slip sheet
10: bolt
11: nut
12: recess
13: recess
14: hole
15: projection
20: drop testing machine
21: drop surface
22: sample stage
23: lower dummy
24: sample
25: upper dummy

The invention claimed is:

1. An apparatus for testing the water hammer strength of a bottle, said apparatus comprising:
   a fixing stage;
   a cushion member on said fixing stage;
   a holding element on said cushion member and configured to hold the bottle at a position above the center of gravity thereof so as to suspend the bottle in the air, the bottle being filled with content and sealed with a cap, at least one of said fixing stage and said holding element having a recess in a surface in contact with said cushion member;
   a weight to be dropped onto the cap of the bottle to apply an impact to the bottle;
   a compression element configured to forcibly push said holding element downward, wherein said cushion member, said holding element, and said compression element are configured such that said compression member compresses and deforms said cushion member via said holding element;
   a first non-slip sheet between said fixing stage and said cushion member; and
   a second non-slip sheet between said cushion member and said holding means;
   wherein at least one of said first non-slip sheet and said second non-slip sheet is arranged in said recess.

2. The apparatus according to claim 1, wherein said compression element comprises a bolt extending from a top surface of said holding element through said holding element and screwed into said fixing stage so as to pull said holding element and said fixing stage together to compress and deform said cushion member therebetween.

3. The apparatus according to claim 1, wherein said cushion member comprises a plurality of cushion bodies bonded together with a non-cushioning plate therebetween.

4. The apparatus according to claim 1, wherein said cushion member is embedded in said recess a distance of 0.2 mm to 0.8 mm.

5. An apparatus for testing the water hammer strength of a bottle, said apparatus comprising:
   a fixing stage;
   a cushion member on said fixing stage, said cushion member comprising a plurality of cushion bodies bonded together with a non-cushioning plate therebetween, an upper non-cushioning plate bonded to an upper end of said cushion member, and a lower non-cushioning plate bonded to a lower end of said cushion member;
   a holding element on said cushion member and configured to hold the bottle at a position above the center of gravity thereof so as to suspend the bottle in the air, the bottle being filled with content and sealed with a cap, at least one of said fixing stage and said holding element having a recess in a surface in contact with said cushion member;
   a weight to be dropped onto the cap of the bottle to apply an impact to the bottle; and
   a compression element configured to forcibly push said holding element downward, wherein said cushion member said holding element, and said compression element are configured such that said compression member compresses and deforms said cushion member via said holding element;
   wherein at least one of said upper non-cushioning plate and said lower non-cushioning plate is arranged in said recess.

6. The apparatus according to claim 5, wherein said compression element comprises a bolt extending from a top surface of said holding element through said holding element and screwed into said fixing stage so as to pull said holding element and said fixing stage together to compress and deform said cushion member therebetween.

7. An apparatus for testing the water hammer strength of a bottle, said apparatus comprising:
   a fixing stage;
   a cushion member on said fixing stage, said cushion member comprising a plurality of cushion bodies bonded together with a non-cushioning plate therebetween, an upper non-cushioning plate bonded to an upper end of said cushion member, and a lower non-cushioning plate bonded to a lower end of said cushion member;
   a holding element on said cushion member and configured to hold the bottle at a position above the center of gravity thereof so as to suspend the bottle in the air, the bottle being filled with content and sealed with a cap;
   a weight to be dropped onto the cap of the bottle to apply an impact to the bottle; and
   a compression element configured to forcibly push said holding element downward, wherein said cushion member, said holding element, and said compression element are configured such that said compression member compresses and deforms said cushion member via said holding element;
   wherein at least one of said upper non-cushioning plate and said lower non-cushioning plate is in contact with a respective one of said holding element and said fixing stage and has a hole in a surface contacting said respective one of said holding element and said fixing stage, and
   wherein said respective one of said holding element and said fixing stage has a projection extending into said hole.

8. The apparatus according to claim 7, wherein said compression element comprises a bolt extending from a top surface of said holding element through said holding element and screwed into said fixing stage so as to pull said holding element and said fixing stage together to compress and deform said cushion member therebetween.

* * * * *